(12) United States Patent
Burkholder et al.

(10) Patent No.: US 9,062,050 B2
(45) Date of Patent: Jun. 23, 2015

(54) INHIBITOR OF JAK1 AND JAK2

(71) Applicant: Eli Lilly and Company, Indianapolis, IN (US)

(72) Inventors: Timothy Paul Burkholder, Carmel, IN (US); Joshua Ryan Clayton, Fishers, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 14/402,146

(22) PCT Filed: Jun. 5, 2013

(86) PCT No.: PCT/US2013/044211
§ 371 (c)(1),
(2) Date: Nov. 19, 2014

(87) PCT Pub. No.: WO2013/188184
PCT Pub. Date: Dec. 19, 2013

(65) Prior Publication Data
US 2015/0133490 A1     May 14, 2015

Related U.S. Application Data

(60) Provisional application No. 61/659,679, filed on Jun. 14, 2012.

(51) Int. Cl.
   *C07D 401/14*     (2006.01)
   *A61K 31/437*     (2006.01)
   *C07D 471/04*     (2006.01)

(52) U.S. Cl.
   CPC ................................. *C07D 471/04* (2013.01)

(58) Field of Classification Search
   CPC ............................. C07D 401/14; A61K 31/437
   USPC .......................................... 514/303; 546/118
   See application file for complete search history.

(56) References Cited

FOREIGN PATENT DOCUMENTS

| WO | WO 2006/087530 A1 | 8/2006 |
|---|---|---|
| WO | WO 2007/140222 A2 | 12/2007 |
| WO | WO 2008/129255 A1 | 10/2008 |

*Primary Examiner* — Niloofar Rahmani
(74) *Attorney, Agent, or Firm* — Robert Brian Johnson

(57) ABSTRACT

The present invention provides an amino pyrazole compound, which is 3-[(1R)-6-fluoro-2,3-dihydro-1H-inden-1-yl]-N-(3-methyl-IH-pyrazol-5-yl)-3H-imidazo[4,5-b]pyridin-5-amine, or a pharmaceutically acceptable salt thereof, that inhibits JAK1 and JAK2 and, therefore may be useful in treating cancer.

6 Claims, No Drawings

INHIBITOR OF JAK1 AND JAK2

The present invention relates to the field of medicine. More particularly, the present invention relates to an amino pyrazole compound, or a pharmaceutically acceptable salt thereof, that inhibits JAK1 and JAK2 and may be useful for treating cancer.

The Janus kinase (JAK) family is a group of tyrosine kinases, and includes JAK1, JAK2, JAK3, and TYK2. The JAK family transmits cytokine-mediated signals into cells by JAK-STAT (Signal Transducer and Activator of Transcription) pathways. One such pathway, JAK-STAT3, is constitutively active in many types of human cancers and cancer cell lines. Constitutively active STAT3 has been implicated in tumor cells for increasing proliferation, survival, and progression.

JAK3 is preferentially expressed in lymphocytes; immunosuppressive effects have been reported for JAK3 inhibitors. Given the immunosuppressive activity of JAK3 inhibitors, inhibition of JAK1 and JAK2, and selectivity against JAK3, would be sought for a JAK inhibitor for use in cancer therapy.

WO 2006/087530 discloses certain pyrazole compounds as inhibitors of tyrosine receptor kinases, and further discloses the compounds as useful in the treatment of cancer.

There remains a need to provide potent, alternative JAK1/2 inhibitors for treatment of solid tumors. There also remains a need to provide potent JAK inhibitors that are selective for JAK1 and JAK2, relative to JAK3. Accordingly, the present invention provides potent inhibitors of JAK1 and JAK2. Also, the present invention provides potent JAK inhibitors that are selective for JAK1 and JAK2 relative to JAK3.

The present invention provides a compound which is 3-[(1R)-6-fluoro-2,3-dihydro-1H-inden-1-yl]-N-(3-methyl-1H-pyrazol-5-yl)-3H-imidazo[4,5-b]pyridin-5-amine, or a pharmaceutically acceptable salt thereof.

As a particular embodiment, the present invention provides the compound which is 3-[(1R)-6-fluoro-2,3-dihydro-1H-inden-1-yl]-N-(3-methyl-1H-pyrazol-5-yl)-3H-imidazo[4,5-b]pyridin-5-amine. As another particular embodiment, the present invention provides the compound which is 3-[(1R)-6-fluoro-2,3-dihydro-1H-inden-1-yl]-N-(3-methyl-1H-pyrazol-5-yl)-3H-imidazo[4,5-b]pyridin-5-amine dihydrochloride.

The present invention provides a pharmaceutical composition comprising 3-[(1R)-6-fluoro-2,3-dihydro-1H-inden-1-yl]-N-(3-methyl-1H-pyrazol-5-yl)-3H-imidazo[4,5-b]pyridin-5-amine, or a pharmaceutically acceptable salt thereof, and a pharmaceutically acceptable carrier, diluent, or excipient. The present invention provides a pharmaceutical composition comprising 3-[(1R)-6-fluoro-2,3-dihydro-1H-inden-1-yl]-N-(3-methyl-1H-pyrazol-5-yl)-3H-imidazo[4,5-b]pyridin-5-amine, and a pharmaceutically acceptable carrier, diluent, or excipient. The present invention provides a pharmaceutical composition comprising 3-[(1R)-6-fluoro-2,3-dihydro-1H-inden-1-yl]-N-(3-methyl-1H-pyrazol-5-yl)-3H-imidazo[4,5-b]pyridin-5-amine dihydrochloride, and a pharmaceutically acceptable carrier, diluent, or excipient.

The present invention provides a pharmaceutical composition comprising 3-[(1R)-6-fluoro-2,3-dihydro-1H-inden-1-yl]-N-(3-methyl-1H-pyrazol-5-yl)-3H-imidazo[4,5-b]pyridin-5-amine, or a pharmaceutically acceptable salt thereof, additionally comprising one or more therapeutic agents.

The present invention provides a method for treating cancer comprising administering to a patient in need thereof an effective amount of 3-[(1R)-6-fluoro-2,3-dihydro-1H-inden-1-yl]-N-(3-methyl-1H-pyrazol-5-yl)-3H-imidazo[4,5-b]pyridin-5-amine, or a pharmaceutically acceptable salt thereof. The present invention provides a method for treating cancer comprising administering to a patient in need thereof an effective amount of 3-[(1R)-6-fluoro-2,3-dihydro-1H-inden-1-yl]-N-(3-methyl-1H-pyrazol-5-yl)-3H-imidazo[4,5-b]pyridin-5-amine. The present invention provides a method for treating cancer comprising administering to a patient in need thereof an effective amount of 3-[(1R)-6-fluoro-2,3-dihydro-1H-inden-1-yl]-N-(3-methyl-1H-pyrazol-5-yl)-3H-imidazo[4,5-b]pyridin-5-amine dihydrochloride.

The present invention provides 3-[(1R)-6-fluoro-2,3-dihydro-1H-inden-1-yl]-N-(3-methyl-1H-pyrazol-5-yl)-3H-imidazo[4,5-b]pyridin-5-amine, or a pharmaceutically acceptable salt thereof, for use in therapy. The present invention provides 3-[(1R)-6-fluoro-2,3-dihydro-1H-inden-1-yl]-N-(3-methyl-1H-pyrazol-5-yl)-3H-imidazo[4,5-b]pyridin-5-amine, or a pharmaceutically acceptable salt thereof, for use in the treatment of cancer. The present invention provides a composition for use in treating cancer, the composition comprising 3-[(1R)-6-fluoro-2,3-dihydro-1H-inden-1-yl]-N-(3-methyl-1H-pyrazol-5-yl)-3H-imidazo[4,5-b]pyridin-5-amine, or a pharmaceutically acceptable salt thereof.

The present invention provides the use of 3-[(1R)-6-fluoro-2,3-dihydro-1H-inden-1-yl]-N-(3-methyl-1H-pyrazol-5-yl)-3H-imidazo[4,5-b]pyridin-5-amine, or a pharmaceutically acceptable salt thereof, in the manufacture of a medicament. The present invention provides the use of 3-[(1R)-6-fluoro-2,3-dihydro-1H-inden-1-yl]-N-(3-methyl-1H-pyrazol-5-yl)-3H-imidazo[4,5-b]pyridin-5-amine, or a pharmaceutically acceptable salt thereof, in the manufacture of a medicament for the treatment of cancer.

The present invention provides 3-[(1R)-6-fluoro-2,3-dihydro-1H-inden-1-yl]-N-(3-methyl-1H-pyrazol-5-yl)-3H-imidazo[4,5-b]pyridin-5-amine in crystalline form. The present invention also provides 3-[(1R)-6-fluoro-2,3-dihydro-1H-inden-1-yl]-N-(3-methyl-1H-pyrazol-5-yl)-3H-imidazo[4,5-b]pyridin-5-amine in crystalline form characterized by a X-ray powder diffraction pattern having characteristic peaks, in 2θ±0.2, occurring at 16.11 and one or more of 4.32, 8.71, 13.12, 15.19, and 18.86.

Furthermore, the present invention provides preferred embodiments of the methods and uses as described herein, in which cancer is selected from the group consisting of breast cancer, lung cancer, pancreatic carcinoma, renal cancer, ovarian cancer, prostate cancer, head and neck cancer, hepatocellular carcinoma, and colon cancer.

As used above, and throughout the description of the invention, the following terms, unless otherwise indicated, shall be understood to have the following meanings:

A "pharmaceutically acceptable carrier, diluent, or excipient" is a medium generally accepted in the art for the delivery of biologically active agents to mammals, e.g., humans.

"Pharmaceutically acceptable salts" refers to the relatively non-toxic, inorganic and organic salts of compounds of the present invention.

"Therapeutically effective amount" or "effective amount" means the amount of the compound, or pharmaceutically acceptable salt thereof, of the present invention or pharmaceutical composition containing a compound, or pharmaceutically acceptable salt thereof, of the present invention that will elicit the biological or medical response of or desired therapeutic effect on a tissue, system, animal, mammal or human that is being sought by the researcher, veterinarian, medical doctor or other clinician.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

The compounds of the present invention are capable of reaction, for example, with a number of inorganic and organic acids to form pharmaceutically acceptable salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

The compounds of the present invention are preferably formulated as pharmaceutical compositions using a pharmaceutically acceptable carrier, diluent, or excipient and administered by a variety of routes. Preferably, such compositions are for oral administration. Such pharmaceutical compositions and processes for preparing them are well known in the art. See, e.g., Remington: The Science and Practice of Pharmacy (A. Gennaro, et al., eds., 21st ed., Mack Publishing Co., 2005).

The amount of the compound of the present invention actually administered will be determined by a physician under the relevant circumstances, including the condition to be treated, the chosen route of administration, the actual compound or compounds of the present invention administered, the age, weight, and response of the individual patient, and the severity of the patient's symptoms. Dosages per day normally fall within the range of about 0.1 to about 300 mg. In some instances, dosage levels below the lower limit of the aforesaid range may be more than adequate, while in other cases still larger doses may be employed. Dosage levels can be determined by one of skill in the art.

The compounds of the present invention, or pharmaceutically acceptable salts thereof, may be prepared by a variety of procedures known in the art, as well as those described in the Examples below. The specific synthetic steps for each of the routes described may be combined in different ways to prepare the compounds of the invention, or pharmaceutically acceptable salts thereof.

The reagents and starting materials are generally readily available to one of ordinary skill in the art. Others may be made by standard techniques of organic and heterocyclic chemistry, techniques which are analogous to the syntheses of known structurally similar active compounds and prodrugs, and the procedures described in the Examples which follow including any novel procedures. The compounds illustrated herein are named and numbered using either ACDLABS or Symyx Draw 3.2.

The compound of Example 1 is named: 3-[(1R)-6-fluoro-2,3-dihydro-1H-inden-1-yl]-N-(3-methyl-1H-pyrazol-5-yl)-3H-imidazo[4,5-b]pyridin-5-amine dihydrochloride; and may also be named 3H-imidazo[4,5-b]pyridin-5-amine, 3-[(1R)-6-fluoro-2,3-dihydro-1H-inden-1-yl]-N-(3-methyl-1H-pyrazol-5-yl)-, dihydrochloride; and other names may be used to unambiguously identify the compound of Example 1. The compound of Example 2 is named: 3-[(1R)-6-fluoro-2,3-dihydro-1H-inden-1-yl]-N-(3-methyl-1H-pyrazol-5-yl)-3H-imidazo[4,5-b]pyridin-5-amine; and may also be named: 3H-imidazo[4,5-b]pyridin-5-amine, 3-[(1R)-6-fluoro-2,3-dihydro-1H-inden-1-yl]-N-(3-methyl-1H-pyrazol-5-yl)-; and other names may be used to unambiguously identify the compound of Example 2.

As used herein, the following terms have the meanings indicated: "DMEA" refers to dimethylethanolamine; "DMF" refers to dimethylformamide; "DMSO" refers to dimethylsulfoxide; "EtOAc" refers to ethyl acetate; "EtOH" refers to ethanol; "ee" refers to enantiomeric excess; "EDTA" refers to ethylenediaminetetraacetic acid; "GC/MS" refers to gas chromatography followed by mass spectroscopy; "LC" refers to liquid chromatography; "LC/MS" refers to liquid chromatography followed by mass spectroscopy; "MeOH" refers to methanol; "MS" refers to mass spectroscopy; "NMR" refers to nuclear magnetic resonance; "PBS" refers to phosphate buffered saline; "TLC" refers to thin layer chromatography; "UV" refers to ultraviolet; and "XRD" refers to X-ray diffraction.

EXAMPLE 1

3-[(1R)-6-fluoro-2,3-dihydro-1H-inden-1-yl]-N-(3-methyl-1H-pyrazol-5-yl)-3H-imidazo[4,5-b]pyridin-5-amine dihydrochloride

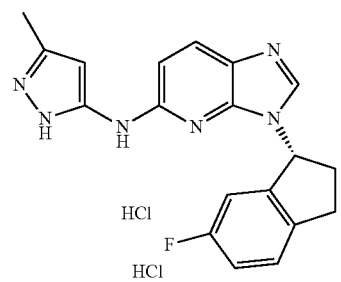 [SMILES: Cc1cc(Nc2ccc3ncn([C@@H]4CCc5ccc(F)cc54)c3n2)[nH]n1 ; Cl ; Cl]

Step 1: Benzyl-(6-fluoroindan-1-ylidene)-amine

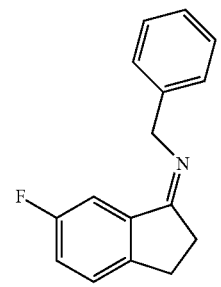 [SMILES: Fc1ccc2c(c1)/C(=N\Cc1ccccc1)CC2]

Combine 6-fluoroindan-1-one (14.57 g, 97.04 mmol) and benzylamine (10.60 mL, 97.04 mmol) in toluene (75 mL). Add p-toluenesulfonic acid monohydrate (0.923 g, 4.85 mmol). Attach a reflux condenser and heat the mixture under nitrogen to reflux over six hours, then stir at room temperature for 14 hours. Extract the mixture with ethyl acetate and water.

Dry the resulting organics with magnesium sulfate, filter, and concentrate in vacuo to give the title compound as a red oil (23.22 g, 100%). MS (ES) m/z=240 [M+1].

Step 2: Benzyl-(6-fluoroindan-1-yl)-amine

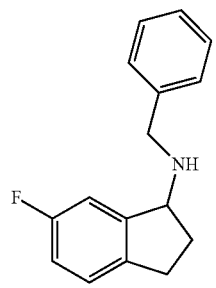 [SMILES: Fc1ccc2c(c1)C(NCc1ccccc1)CC2]

Dissolve benzyl-(6-fluoroindan-1-ylidene)-amine (23.22 g, 97.03 mmol) in ethanol (1200 mL). Cool the mixture to 0° C. under nitrogen. Add sodium borohydride (11.01 g, 291.10 mmol) to the mixture. After one hour, add dichloromethane (150 mL) and water (150 mL). Stir for 14 hours under nitrogen and concentrate in vacuo to remove ethanol. Extract the residue with dichloromethane and saturated aqueous sodium chloride. Dry the resulting organics with magnesium sulfate, filter, and concentrate in vacuo to give the title compound as a red oil (22.12 g, 94%). MS (ES) m/z=242 [M+1].

Step 3: 6-fluoroindan-1-ylamine

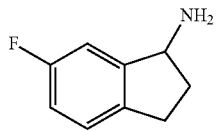 [SMILES: NC1CCc2ccc(F)cc21]

To a high-pressure flask, add 10% palladium on carbon (1.44 g) in ethanol (100 mL). Add a solution of benzyl-(6-fluoroindan-1-yl)-amine (14.44 g, 59.84 mmol) in ethanol (200 mL). Purge the chamber with nitrogen three times, and then with hydrogen three times. Stir vigorously under hydrogen (60 psi) at 50° C. for two hours. Filter the mixture through Celite® 521 and wash the solids with methanol. Concentrate the filtrate in vacuo to give the title compound as a light brown liquid (9.14 g, 100%). MS (ES) m/z=152 [M+1].

Step 4: 6-Chloro-N-(6-fluoro-2,3-dihydro-1H-inden-1-yl)-3-nitropyridin-2-amine

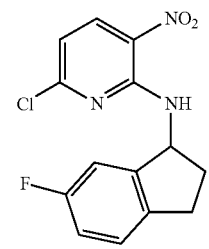 [SMILES: O=[N+]([O-])c1ccc(Cl)nc1NC1CCc2ccc(F)cc21]

Dissolve 6-fluoroindan-1-ylamine (8.50 g, 56.22 mmol) in methanol (200 mL) and triethylamine (8.62 mL, 61.84 mmol). Add 2,6-dichloro-3-nitropyridine (10.85 g, 56.22 mmol) and stir under nitrogen for 14 hours. Filter the reaction mixture and wash the solids with methanol and hexanes to give the title compound as a yellow solid (9.00 g, 52%). MS (ES) m/z=308 [M+1].

Step 5: N2-(6-fluoroindan-1-yl)-N6-(5-methyl-2H-pyrazol-3-yl)-3-nitropyridine-2,6-diamine

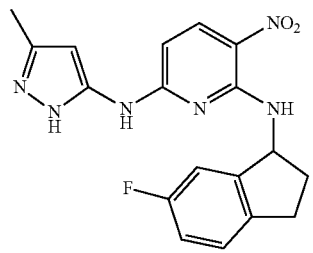 [SMILES: Cc1cc(Nc2ccc([N+](=O)[O-])c(NC3CCc4ccc(F)cc43)n2)[nH]n1]

Combine 6-chloro-N-(6-fluoro-2,3-dihydro-1H-inden-1-yl)-3-nitropyridin-2-amine (9.00 g, 29.34 mmol) and 3-amino-5-methylpyrazole (4.56 g, 46.95 mmol) in dimethylsulfoxide (60 mL). Add N,N-diisopropylethylamine (8.18 mL, 46.95 mmol) and heat the reaction under nitrogen at 120° C. for 90 minutes. Pour the reaction into ice water (200 mL) and stir 20 minutes, then filter. Suspend the solid obtained in a mixture of dichloromethane and methanol and stir at 40° C. for 20 minutes. Filter the mixture to give the title compound as a yellow solid (6.03 g, 56%). MS (ES) m/z=369 [M+1].

Step 6: 3-[(1R)-6-fluoro-2,3-dihydro-1H-inden-1-yl]-N-(3-methyl-1H-pyrazol-5-yl)-3H-imidazo[4,5-b]pyridin-5-amine

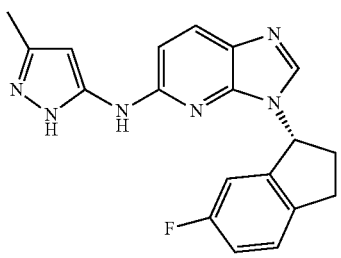 [SMILES: Cc1cc(Nc2ccc3ncn([C@@H]4CCc5ccc(F)cc54)c3n2)[nH]n1]

Dissolve N2-(6-fluoroindan-1-yl)-N6-(5-methyl-2H-pyrazol-3-yl)-3-nitropyridine-2,6-diamine (0.571 g, 1.55 mmol) in methanol (10 mL). Add indium (0.890 g, 7.75 mmol) and hydrochloric acid (12N, 0.65 mL, 7.75 mmol). Stir the mixture under nitrogen for one hour. Filter the reaction mixture through Celite® 521 and wash the solids with methanol. Concentrate the filtrate in vacuo to afford crude N2-(6-fluoroindan-1-yl)-N6-(5-methyl-2H-pyrazol-3-yl)-pyridine-2,3,6-triamine dihydrochloride.

Dissolve N2-(6-fluoroindan-1-yl)-N6-(5-methyl-2H-pyrazol-3-yl)-pyridine-2,3,6-triamine dihydrochloride in acetic acid (5 mL) and trimethyl orthoformate (0.68 mL, 6.20 mmol). Stir under nitrogen for 30 minutes. Concentrate in vacuo and purify by reverse phase chromatography, eluting with a gradient of 0.03% aqueous hydrochloric acid in acetonitrile to give the racemate of the title compound (0.124 g, 19%, 2 steps). MS (ES) m/z=349 [M+1]. Separate the racemate with chiral chromatography conditions to give the title compound: (70 mg, 11%. Enantiomer 1 (first eluent at 3.7 min)>99% ee, 100% MeOH, 0.2% DMEA, 1.0 mL/min, 4.6× 150 mm, CHIRALPAK® AD-H).

Step 7: 3-[(1R)-6-fluoro-2,3-dihydro-1H-inden-1-yl]-N-(3-methyl-1H-pyrazol-5-yl)-3H-imidazo[4,5-b]pyridin-5-amine dihydrochloride

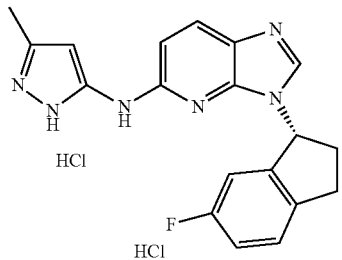 [SMILES: Cc1cc(Nc2ccc3ncn([C@@H]4CCc5ccc(F)cc54)c3n2)[nH]n1 ; Cl ; Cl]

Dissolve 3-[(1R)-6-fluoro-2,3-dihydro-1H-inden-1-yl]-N-(3-methyl-1H-pyrazol-5-yl)-3H-imidazo[4,5-b]pyridin-5-amine (0.070 g, 0.201 mmol) in dichloromethane (5 mL). Add hydrogen chloride, 4 M in 1,4-dioxane (0.100 mL, 0.400 mmol). Stir the solution for 14 hours, and then concentrate to dryness in vacuo. Dissolve in methanol and concentrate to dryness in vacuo three times to give the title compound (0.067 g, 79%). MS (ES) m/z=349 [M+1].

EXAMPLE 2

3-[(1R)-6-fluoro-2,3-dihydro-1H-inden-1-yl]-N-(3-methyl-1H-pyrazol-5-yl)-3H-imidazo[4,5-b]pyridin-5-amine

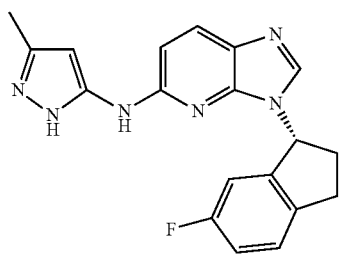 [SMILES: Cc1cc(Nc2ccc3ncn([C@@H]4CCc5ccc(F)cc54)c3n2)[nH]n1]

Step 1: (1S)-6-fluoro-2,3-dihydro-1H-inden-1-ol

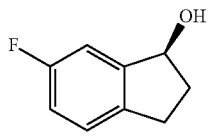 [SMILES: O[C@H]1CCc2ccc(F)cc21]

Equip a 22 L 4-necked, round-bottom flask with overhead agitation, thermocouple, 1 L and 5 L addition funnels, cooling bath, and nitrogen inlet. Under a nitrogen purge, charge the flask with 6-fluoro-2,3-dihydro-1H-inden-1-one (500 g, 3.33 moles) and toluene (5 L). Stir the resulting mixture for 5 minutes to dissolve all solids, and then cool to −10° C. using an ice/acetone bath. Charge the 1 L addition funnel with R-(−)-2-methyl-CBS-oxazaborolidine (1M in toluene, 666 mL, 0.666 mol). Add the solution to the reaction mixture, and then stir for 5 minutes. Charge the 5 L addition funnel with toluene (5 L) followed by borane-methyl sulfide complex (310.1 mL, 3.33 mol). After swirling the funnel to mix the reagents, add this solution dropwise to the reaction mixture over 3 hours, maintaining the pot temperature below −5° C. After 15 minutes, monitor a sample of the reaction by TLC (quench 25 μL reaction mix with 50 μL MeOH; 75/25 hexanes/EtOAc, UV). This analysis shows no starting material remaining. Allow the mixture stir in the cold bath overnight.

Cool the reaction mixture to 10° C., and charge methanol (0.5 L) to the addition funnel, then add drop-wise over 30 minutes. Off-gassing is evident at the beginning of the MeOH quench, but subsides after ~⅓ of the addition. Stir the resulting mixture for 15 minutes and then dilute with saturated NaCl (2.5 L). After stirring for 20 minutes, filter the mixture across a pad of Hyflo Super Cel® and rinse the pad with toluene (2 L).

Transfer the filtrate to a bottom outlet flask and the separate the layers. Wash the organic with de-ionized water (2.5 L), 1N HCl (2.5 L), saturated NaHCO₃ (2.5 L), and saturated NaCl (2.5 L). After drying over Na₂SO₄ (1 kg) in the presence of Darco (0.5 kg) for 0.5 h, filter the mixture across Hyflo Super Cel® topped with Kieselgel 60 silica (0.5 kg). Rinse the pad with toluene (1 L) and concentrate the filtrate in vacuo. Seed the resulting oil with previously made solid to induce crystallization. The crystallization provides the title compound as a pale yellow solid (500 g, 98.7%, 98.1% ee). ¹H NMR (CDCl₃, 500.0 MHz): δ 1.74 (bs, 1H), 1.99 (m, 1H), 2.54 (m, 1H), 2.77 (m, 1H), 3.00 (m, 1H), 5.22 (m, 1H), 6.95 (td, 1H), 7.09 (dd, 1H), 7.17 (td, 1H) ppm.

Step 2:
(1R)-1-Azido-6-fluoro-2,3-dihydro-1H-indene

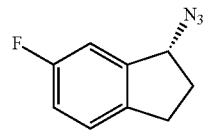

Equip a 22 L 3-neck flask with overhead agitation, thermocouple, nitrogen inlet, 1 L addition funnel, and cooling bath. Charge the flask with (1S)-6-fluoro-2,3-dihydro-1H-inden-1-ol (700 g, 4.6 moles) and toluene (7 L). Cool the resulting solution to 0-5° C. and add diphenylphosphoryl azide (1444 g, 5.1 mol) in one portion. After 15 minutes, charge 1,8-diazabicyclo[5.4.0]-undec-7-ene (847 mL, 5.5 mol) to the addition funnel, then add drop-wise to the reaction vessel over 2 hours, keeping the pot temperature below 10° C. Remove the bath and allow the reaction mixture to stir overnight at ambient temperature.

After 22 hours, TLC (80/20 hexane/EtOAc, UV) and GC/MS indicate the reaction is complete. Add de-ionized water (3.5 L) over 15 minutes and stir for 15 minutes. Transfer the mixture to a bottom outlet flask and separate the layers. Wash the organics with de-ionized water (3.5 L), then 0.5 M HCl (3.5 L), and finally de-ionized water (3.5 L). Combine the three aqueous washes and back-extract with toluene (3.5 L). Combine the organics and dry over Na₂SO₄ (1 kg) in the presence of Darco (0.5 kg). After stirring for 15 minutes, filter the mixture across GFF paper topped with a pad of Hyflo Super Cel®. Rinse the pad with toluene (1 L), and transfer the filtrate to a 22 L Büchi flask and concentrate in vacuo to ~4 volumes (2.8 L).

Set up a large funnel for silica gel plug chromatography and charge with Kieselgel 60 silica (6 Kg). Top the silica with sand (1 Kg) and wet with toluene. Pour the 2.8 L of reaction solution containing the crude product onto the funnel under slight vacuum. Elute the product with toluene (4×4 L). Transfer the filtrate to a tared flask and concentrate in vacuo (40° C. bath) to about 3 L (2788 g of toluene solution). Based on small sample weight analysis (0.123 g of title compound in 0.467 g of toluene solution), there are 753.5 g of title compound (7782 g solution in toluene, 90.2% yield). Transfer the toluene solution to a gallon jug and store in the refrigerator for use in the subsequent step.

Step 3: (1R)-6-fluoro-2,3-dihydro-1H-inden-1-amine

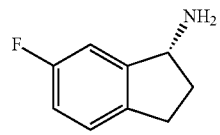 [SMILES: N[C@@H]1CCc2ccc(F)cc21]

Charge a 3-gallon Hydro tank T-85 with 5% Pd/C (8.2 g in 164 mL toluene) and a third of the (1R)-1-azido-6-fluoro-2,3-dihydro-1H-indene (163.9 g azide in 2594 g of ethanol solution) obtained in Step 2. Purge the tank with nitrogen and then pressurize with hydrogen (~50 psi). Stir the mixture for 30 minutes. Then vent the tank and re-charge with hydrogen (~50 psi) and stir for another 30 minutes. TLC and GC/MS show that the reaction is complete. Transfer the reaction mixture to a carboy and rinse the tank with 3A-EtOH. Repeat the reaction at the same scale twice. Combine the solution of three reactions. Concentrate under reduced pressure to about 8 volumes. Filter the mixture by GFF paper to remove the catalyst and rinse the pad with 3A-EtOH (~200 mL). Based on the analysis of a small sample, the title compound is obtained in an 3A-EtOH solution in 92% yield (386 g).

Step 4: 6-Chloro-N-[(1R)-6-fluoro-2,3-dihydro-1H-inden-1-yl]-3-nitropyridin-2-amine

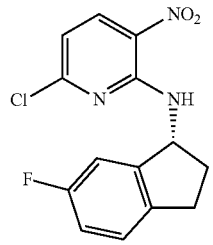 [SMILES: O=[N+]([O-])c1ccc(Cl)nc1N[C@@H]1CCc2ccc(F)cc21]

Purge a 12 L 3-necked flask with nitrogen, and then assemble thermocouple, heating mantle and condenser. Charge (1R)-6-fluoro-2,3-dihydro-1H-inden-1-amine (386 g, 2.55 mol) to the flask, add 3A-EtOH (3.9 L), diisopropylethylamine (1.34 L, 7.68 mol), and 2,6-dichloro-3-nitropyridine (643 g, 3.07 moles). Stir the reaction mixture at ambient temperature for eight hours followed by heating to 70° C. for 12 hours. Cool the reaction mixture to 8° C. over 1.25 h, then filter onto a polypropylene pad. Wash the solids with 3A-EtOH (760 mL), transfer to a tared dish and further dry in a vacuum oven (45° C.) to afford the title compound as an orange solid (786 g, 71%, 98.0% ee). GC/MS (m/z): 307 (M+).

Step 5: N2-[(1R)-6-fluoro-2,3-dihydro-1H-inden-1-yl]-N6-(5-methyl-1H-pyrazol-3-yl)-3-nitropyridine-2,6-diamine

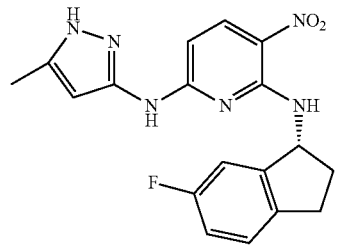 [SMILES: Cc1cc(Nc2ccc([N+](=O)[O-])c(N[C@@H]3CCc4ccc(F)cc43)n2)n[nH]1]

Equip a 3 neck flask (22 L) with a thermocouple, condenser, overhead stirrer, N₂ inlet, and heating mantle. To the flask, charge 6-chloro-N-[(1R)-6-fluoro-2,3-dihydro-1H-inden-1-yl]-3-nitropyridin-2-amine (600 g, 1.95 mol), 5-methyl-1H-pyrazol-3-amine (208.31 g, 2.14 mol), dimethylsulfoxide (6.0 L), and diisopropylethylamine (680.11 mL, 3.90 moles). Stir the solution at 70° C. for 20 hours. Cool the mixture to ambient temperature and dilute it with MeOH (6.0 L). Add de-ionized water (2.1 L) to the solution over one hour to give in an orange suspension. Stir the suspension for one hour, and then filter through polypropylene. Wash the filter cake with de-ionized water (12 L), transfer the solid to a tared dish and vacuum-dry (50° C.) to constant weight to provide the title compound (647 g, 90%). MS (m/z): 369 (M+1).

Step 6: 3-[(1R)-6-fluoro-2,3-dihydro-1H-inden-1-yl]-N-(3-methyl-1H-pyrazol-5-yl)-3H-imidazo[4,5-b]pyridin-5-amine

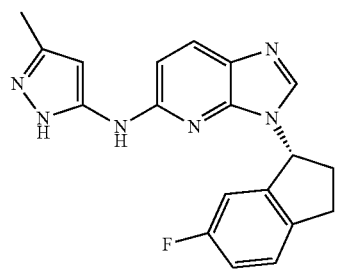 [SMILES: Cc1cc(Nc2ccc3ncn([C@@H]4CCc5ccc(F)cc54)c3n2)[nH]n1]

Add N2-[(1R)-6-fluoro-2,3-dihydro-1H-inden-1-yl]-N6-(5-methyl-1H-pyrazol-3-yl)-3-nitropyridine-2,6-diamine (622 g, 1.69 mol) in 10 L round-bottom flask and treat it with DMF (5 L). Swirl the flask contents until all solids dissolve. Charge trimethylorthoformate (1.85 L, 16.9 mol) and pyridinium p-toluenesulfonate (42.4 g, 0.169 mol) to the flask with swirling. Charge the 3-gallon hydro tank T-85 with 5% Pd/C (93.3 g, 15 weight % load) as a thick slurry in DMF (100 mL) under a nitrogen purge. Add the above mixture to the hydro tank, and purge with nitrogen several times, and then charge the tank under hydrogen (~50 psi). Heat the mixture to 60° C. and allow to stir overnight. At about 22 hours, vent the reactor, take a sample and check by TLC and LC/MS, both of which indicate the reaction is complete. Filter the mixture through a pad of Hyflo Super Cel® and rinse the tank and pad with EtOAc (1 L). Transfer the filtrate to a Büchi flask, dilute with de-ionized water (622 mL) and concentrate in vacuo (50° C. bath) to remove excess trimethylorthoformate. Transfer the DMF solution to a 50 L bottom outlet flask and dilute with EtOAc (12.4 L). Wash the solution with saturated LiCl solution (3×6.22 L). Combine the aqueous washes and back-extract with EtOAc (4×3.11 L). Combine the organics and wash with saturated LiCl (2×1 L), dry over $Na_2SO_4$ and filter through GFF paper. Concentrate the filtrate in vacuo (45° C. bath) to afford crude product as a green solid (609 g, 103.5%). 1H NMR (DMSO-d6, 500.0 MHz): δ 2.15 (s, 3H), 2.67 (q, 2H), 2.99 (m, 1H), 3.17 (m, 1H), 5.89 (s, 1H), 6.11 (t, 1H), 6.76 (dd, 1H), 6.87 (d, 1H), 7.10 (td, 1H), 7.42 (m, 1H), 7.76 (d, 1H), 7.99 (s, 1H), 9.23 (bs, 1H), 11.65 (bs, 1H) ppm.

Equip a 3 necked flask (22 L) with a thermocouple, condenser, overhead stirrer, $N_2$ inlet, and heating mantle. To the flask, charge the crude material, made directly above, (598.5 g, 1.7 mol) and acetonitrile (12 L) and heat the resulting mixture to reflux. Upon reaching a complete solution, stop the heat source and allow the solution to self-cool. Seed the solution with the green solid from above at 56° C. and crystallization begins immediately; initial seed material is obtained essentially as above. Further cool the suspension with an ice bath, stir overnight, and filter. Wash the product cake with acetonitrile (1.2 L), transfer the solids to a tared dish, and dry under vacuum (50° C.) to constant weight to give the title compound (349.54 g, 58.4%). $^1$H NMR (DMSO-d6, 500.0 MHz): δ 2.15 (s, 3H), 2.67 (q, 2H), 2.99 (m, 1H), 3.17 (m, 1H), 5.89 (s, 1H), 6.11 (t, 1H), 6.76 (dd, 1H), 6.87 (d, 1H), 7.10 (td, 1H), 7.42 (m, 1H), 7.76 (d, 1H), 7.99 (s, 1H), 9.23 (bs, 1H), 11.65 (bs, 1H) ppm.

X-Ray Powder Diffraction

The XRD patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.85 and 26.77 degrees 2-theta.

Thus, a prepared sample of Example 2 is characterized by an XRD pattern using CuKa radiation as having diffraction peaks (2-theta values) as described in Table 1 below. Specifically the pattern contains a peak at 16.11 in combination with one or more of the peaks selected from the group consisting of 4.32, 8.71, 13.12, 15.19 and 18.86 with a tolerance for the diffraction angles of 0.2 degrees.

TABLE 1

X-ray powder diffraction peaks of Example 2.

| Peak | Angle (2-Theta °) | Intensity (%) |
|---|---|---|
| 1 | 4.32 | 30 |
| 2 | 6.95 | 19 |
| 3 | 8.71 | 23 |
| 4 | 12.21 | 14 |
| 5 | 13.12 | 34 |
| 6 | 13.29 | 23 |
| 7 | 15.19 | 48 |
| 8 | 16.11 | 100 |
| 9 | 17.66 | 20 |
| 10 | 18.86 | 62 |
| 11 | 18.98 | 46 |
| 12 | 19.49 | 74 |
| 13 | 20.25 | 35 |
| 14 | 21.94 | 16 |
| 15 | 24.02 | 33 |

JAK1/2/3 In Vitro Enzyme Assays

The JAK LanthaScreen™ Kinase Assay (Life Technologies, #PV4844) is used to determine compound $IC_{50}$ values against the JAK1, JAK2, and JAK3 kinases. This kinase assay is a Time Resolved Fluorescence Resonance Energy Transfer (TR-FRET) assay format that uses long-lifetime terbium (Tb) labeled antibody as the donor species and Green Fluorescent Protein-Signal Transducers and Activators of Transcription (GFP-STAT1) as the acceptor species.

The TR-FRET ratio is used to monitor JAK1, JAK2, or JAK3 activity where an increase in phosphorylation of the GFP-STAT1 results in an increase in the TR-FRET ratio. Perform the kinase reaction using a 12.5 microliter reaction volume in shallow black 384-well Proxiplate (PerkinElmer, #6008260). Add reagents to obtain final reaction conditions of 50 millimolar N-2-hydroxyethylpiperazine-N-2'-ethanesulfonic acid (HEPES) pH 7.3, 1.76 millimolar Triton™ X-100, 20.0 micromolar adenosine triphosphate (ATP) for JAK1 assay (5 micromolar ATP for JAK2 assay, or 2 micromolar ATP for JAK3 assay), 10.0 millimolar magnesium chloride ($MgCl_2$), 1 millimolar ethylene glycol tetraacetic acid (EGTA), 0.01% Brij-35, 0.05 micromolar Green Fluorescent Protein-Signal Transducers and Activators of Transcription (GFP-STAT1), 14 nanomolar JAK1 enzyme (or 1.0 nanomolar JAK2 enzyme, or 2.5 nanomolar JAK3 enzyme) and 4% dimethysulfoxide and serial dilutions of compound of Example 1 (diluted 1:3 from 20,000 to 1 nanomolar). Following ATP/GFP-STAT1 addition, centrifuge the assay plates for 1 minute at 1000 revolutions per minute (RPM). Allow the plates to incubate at room temperature for 60 minutes, and then stop with the addition of 12.5 microliters of a stopping buffer containing 20 millimolar ethylenediaminetetraacetic acid (EDTA), 2 nanomolar Tb-anti-pSTAT1[pTyr701], 0.67 millimolar tris(hydroxymethyl)aminoethane hydrochloride (Trizma®) pH 7.5, 0.02% sodium azide and 0.01% nonylphenylpolyethylene glycol (Nonidet® P40). Incubate at room temperature for 90 minutes, and read in an EnVision plate reader (PerkinElmer, #2104-0010) with 340 nm wavelength excitation filter and emission filters of 520 nm and 495 nm wavelengths. The ratio is derived from the emission wavelength for the GFP-STAT1 which is measured at 520 nanometer versus the emission at 495 nanometer for the Tb-anti-pSTAT1[pTyr701]. Derive the $IC_{50}$ value for the compound using percent inhibition data, which is calculated from the reaction data relative to on-plate controls (active enzyme versus 2.0 micromolar control-inhibited enzyme). Use ActivityBase 4.0 to fit the percent inhibition and ten-point compound concentration data to a four-parameter logistic equation.

A compound within the scope of the invention is tested in this assay substantially as described above. The compound of Example 1 is determined to have an $IC_{50}$ of 1.7 nM+/−0.8 nM against JAK1 (n=3), an $IC_{50}$ of 1.7 nM against JAK2 (n=1), and an $IC_{50}$ of 8.0 nM+/−5.9 nM against JAK3 (n=6). The compound of Example 1 demonstrated greater than four-fold selectivity for JAK1 and JAK2 over JAK3 in the enzyme assays. These results show that the compound of Example 1 is a potent in vitro inhibitor of JAK1 and JAK2, and is selective in vitro for JAK1 and JAK2 over JAK3.

JAK2 EPO-TF UpSTAT5 Cell-Based Assay—Cellomics ArrayScan® HCS

The JAK2 EPO-TF1/pSTAT5 cell-based assay mimics the constitutive activation of JAK2-STAT5 in erythroid progenitor cells, which drives the overproduction of red blood cells, a marker of polycythemia vera (PV). Therefore, the EPO-TF1/pSTAT5 cell-based assay enables the evaluation of the JAK2 cellular activity of JAK compounds in vitro.

TF-1 (human erythroid leukemia) cells are maintained in RPMI 1640 (RPMI-1640 was developed by Moore et. al. at Roswell Park Memorial Institute. The formulation is based on the RPMI-1630 series of media utilizing a bicarbonate buffering system and alterations in the amounts of amino acids and vitamins.) with 10% fetal bovine serum (FBS), 0.075% sodium bicarbonate, 1 mM sodium pyruvate, 1× antibiotic/antimycotic (Invitrogen, Carlsbad, Calif.) and 0.45% glucose. The medium is supplemented with GM-CSF (granulocyte-macrophage colony-stimulating factor) at a final concentration of 2 ng/mL. Cells are kept at 37° C. with 5% $CO_2$. Cells are starved in serum free medium to remove endogenous growth factors. TF-1 cells are counted and cells are collected to seed $2 \times 10^7$ cells per 96-well plate at a density of $2 \times 10^5$ cells per well. The cells are rinsed twice with unsupplemented RPMI 1640 (RPMI 1640 with 0.075% sodium bicarbonate, 1 mM sodium pyruvate, 1× antibiotic/antimycotic, and 0.45% glucose) before suspending cells at a final concentration of $5 \times 10^5$ cells/mL in RPMI with 0.6% FBS. The diluted cells are added back to tissue culture flasks and incubated overnight at 37° C. Test compound is prepared in 100% DMSO at 10 mM concentration. Compound is serially diluted 1:3 with 100% DMSO in a 10 point-200× concentration-response range (4 mM-200 nM). In a separate 96 deep well plate 2.5 µL of 200× compound solution is added to 125 µL of complete RPMI 1640 media with 10% FBS for a 4× concentration compound plate.

To perform the assay, serum-starved cells are collected and washed once with unsupplemented RPMI 1640 medium. Cells are suspended in 10% FBS complete RPMI medium for a final concentration of $8 \times 10^5$ cells/mL. An aliquot of 250 µL of diluted cells ($2 \times 10^5$ cells) are added to each well in the 4× concentration compound plate. Cells are mixed by vortexing and the plate is incubated in a 37° C. water bath for 10 min. A fresh 4× working solution of Erythropoietin (EPO) at 6.4 Units/mL is prepared by using pre-warmed 10% FBS complete RPMI 1640 medium. After the cells are treated with compound for 10 min, 125 µL of EPO medium is added into each well and the plate is vortexed. Cells are incubated in a 37° C. water bath for 20 min and mixed every 5 min during the incubation time. Final 10 point concentration-response range is 20 µM-1 nM at a final concentration of DMSO at 0.5% and EPO at 1.6 U/mL. After cell treatment, 500 µL of 1% formaldehyde solution (made freshly with phosphate-buffered saline (PBS) and kept warm at 37° C.) is added to each well. Plates are sealed and inverted 8-10 times to mix. Plates are placed in a 37° C. water bath for 10 min. After incubation, cell plates are spun at 1200 rpm for 5 min at room temperature (RT). The supernatant is aspirated, leaving 100 µL of cells ($2 \times 10^5$ cells). The cells are vortexed and washed twice with 800 µL of PBS by repeating the spin steps and leaving 100 µL containing $\sim 2 \times 10^5$ cells after the final wash. An aliquot of 800 µL of cold 90% methanol is added to the cells and placed at −20° C. overnight. Plates are spun and methanol is removed. Cells are washed with FACS buffer (PBS with 5% FBS and 0.02% sodium azide). An aliquot of 200 µL of 1 to 10 dilution of Mouse anti-pSTAT5 (pY694) Alexa Fluor 647® in fluorescence activated cell sorting (FACS) buffer is added to the cells. Cells are mixed well and incubated at RT in the dark for 2 h. Cells are washed once with PBS and 100 µL of cells are left. A working solution of 2 µg/mL Hoechst (Acros Organics, Morris Plains, N.J.) is prepared with PBS. An aliquot of 200 µL is added to each well and cells are incubated at RT in the dark for 10 min. Cells are washed with PBS, and 50 µL of Cytofix (BD Biosciences, San Jose, Calif.) is added to the cells. The cells are transferred to 96 well black tissue culture plates and sealed. The plates are spun down. Mean fluorescent intensity data are collected and analyzed using Cellomics Arrayscan® VTi. Compound treatment is compared to the vehicle to determine percent inhibition data. The relative $IC_{50}$ is calculated using a 4 parameter logistic curve fitting analysis with ActivityBase 4.0.

A compound within the scope of the invention is tested in this assay substantially as above. The compound of Example 1 inhibits JAK2 with an $IC_{50}$ of 0.035 µM+/−0.013 µM (n=65). These results show that the compound of Example 1 is a potent inhibitor of JAK2 in the JAK2 EPO-TF 1/pSTAT5 cell-based assay.

JAK3 IL-2-NK-92/pSTAT5 Cell-Based Assay—Cellomics ArrayScan® HCS

IL-2 activates the JAK3 pathway in natural killer (NK) cells to drive the NK and CD8 lymphocyte proliferation. Therefore, IL-2 stimulated NK92/pSTAT5 cell-based assay enables the evaluation of the JAK3 cellular activity of JAK compounds in vitro.

NK-92 (natural killer) cells (ATCC, Manassas, Va.) are maintained in minimum essential medium (MEM) Alpha with 15% fetal bovine serum, 15% Horse Serum and 1× antibiotic/antimycotic (Invitrogen, Carlsbad, Calif.). The medium is supplemented with IL-2 (R&D systems, Minneapolis, Minn.) for a final concentration of 4 ng/mL. Cells are kept at 37° C. with 5% $CO_2$. Cells are starved in serum free medium to remove endogenous growth factors. NK-92 cells are counted and collected to seed $2 \times 10^7$ cells per 96-well plate at a density of $2 \times 10^5$ cells per well. The cells are rinsed twice with unsupplemented MEM Alpha (MEM Alpha) before suspending cells at a final concentration of $8 \times 10^5$ cells/mL in MEM Alpha with 0.6% serum (0.3% FBS, 0.3% horse serum). The diluted cells are added back to tissue culture flasks and incubated overnight at 37° C. Test compound is prepared in 100% DMSO at 10 mM concentration. Compound is serially diluted 1:3 with 100% DMSO in a 10 point-200× concentration-response range (4 mM-200 nM). In a separate 96 deep well plate 2.5 µL of 200× compound solution is added to 125 µL of 10% FBS complete RPMI 1640 medium for a 4× concentration compound plate. To perform the assay, serum-starved cells are collected and washed once with unsupplemented RPMI 1640 medium. Cells are suspended in 10% FBS complete RPMI 1640 medium for a final concentration of $8 \times 10^5$ cells/mL. An aliquot of 250 µL of diluted cells ($2 \times 10^5$ cells) is added to each well in the 4× concentration compound plate. Cells are mixed by vortexing and the plate is incubated in a 37° C. water bath for 10 min. A fresh 4× working solution of IL-2 at 2 ng/mL is prepared using pre-warmed 10% FBS complete RPMI medium. After the cells are treated with compound for 10 min, 125 µL of IL-2 medium is added into each well. Cells are mixed by vortexing. Cells are incubated in a 37° C. water bath for 20 min and mixed every 5 min during the incubation time. Final 10 point concentration-response range is 20 µM-1 nM at a final concentration of DMSO at 0.5% and IL-2 at 0.5 ng/mL. After cell treatment, 500 µL of 1% formaldehyde solution (made freshly with phosphate-buffered saline (PBS) and kept warm at 37° C.) is added to each well. Plates are sealed and inverted 8-10 times to mix. Plates are placed in a 37° C. water bath for 10 min. After incubation, cell plates are spun at 1200 rpm for 5 min at RT. The supernatant is aspirated, leaving 100 µL of cells ($2 \times 10^5$ cells). The cells are vortexed and washed twice with 800 µL of PBS by repeating the spin steps and leaving 100 µL containing ~$2 \times 10^5$ cells after the final wash. An aliquot of 800 µL of cold 90% methanol is added to the cells and placed at −20° C. overnight. Plates are spun and methanol is removed. Cells are washed with FACS buffer (PBS with 5% FBS and 0.02% sodium azide). An aliquot of 200 µL of 1 to 10 dilution of Mouse anti-pSTAT5 (pY694) Alexa Fluor 647® in fluorescence activated cell sorting (FACS) buffer is added to the cells. Cells are mixed well and incubated at RT in the dark for 2 h. Cells are washed once with PBS and 100 uL of cells are left. A working solution of 2 µg/mL Hoechst (Acros Organics, Morris Plains, N.J.) is prepared with PBS. An aliquot of 200 µL is added to each well and cells are incubated at RT in the dark for 10 min. Cells are washed with PBS, and 50 µL of Cytofix® (BD Biosciences, San Jose, Calif.) is added to the cells. The cells are transferred to 96 well black tissue culture plates and sealed. The plates are spun down. Mean fluorescent intensity data are collected and analyzed using Cellomics Arrayscan® VTi. Compound treatment is compared to the vehicle to determine percent inhibition data. The relative $IC_{50}$ is calculated using a 4 parameter logistic curve fitting analysis with ActivityBase 4.0.

A compound within the scope of the invention is tested in this assay substantially as above. The compound of Example 1 inhibits JAK3 with an $IC_{50}$ of 0.228 µM+/−0.076 µM (n=61). From the results of the two cell-based assays above, the ratio of JAK3/JAK2, the $IC_{50}$ was determined to be more than six-fold, which demonstrates that the compound of Example 1 is selective for JAK2 over JAK3 in the JAK2 EPO-TF 1/pSTAT5 and JAK3 IL-2-NK-92/pSTAT5 cell-based assays.

DS1-AlphaScreen-pSTAT3-Cell-Based Assay

The DS1-AlphaScreen-pSTAT3-cell-based assay is used to examine the potency of compounds at blocking the IL6-stimulated STAT3 pathway. The JAK-STAT3 pathway is constitutively active in many types of cancers and is implicated in tumor cells for increasing proliferation, survival, and invasion. DS1 cells (ATCC) are cultured in RPMI complete medium with 10% FBS and then adopted and grown in DMEM/High Modified medium supplemented with 10% FBS at 37° C. at 95% humidity and under an atmosphere of 5% $CO_2$. DS1 cells are plated at a density of $4 \times 10^4$ cells/well in 96 well-plates and cultured in serum-free culture medium at 37° C. for three hours, followed by pre-treatment either with vehicle alone (DMSO) or test compounds across a range of final concentrations from 0-20 µM for 10 min. IL6 (R&D System, 206-IL) is then added into the cell culture at 10 ng/ml final concentration, which is continued for an additional 30 min at 37° C. Finally, cells are lysed with 5× alpha lysis buffer and transferred to a 384-well plate (PerkinElmer, #6008280) filled with the reaction mixture (TGR Biosciences, South Australia, Australia, #TGRS3S10K) for pSTAT3 detection (#TGRS3SHV100). The plates are sealed and incubated at room temperature for 2 hours, and pSTAT3 is measured by using an Envision06 plate reader (TGR Biosciences, South Australia, Australia). The data are analyzed with Activity-Base 4.0.

A compound within the scope of the invention is tested in this assay substantially as above. The compound of Example 1 inhibits IL-6-STAT3 signaling with an IC50 of 0.066+/−0.023 µM. These results demonstrate that the compound of Example 1 inhibits the IL-6 stimulated JAK-STAT3 pathway in the DS1-AlphaScreen-pSTAT3-cell-based assay.

Mia-Paca2-MSD-pSTAT3 Cell-Based Assay

The Mia-Paca2-MSD (MesoScale Diagnostics)-pSTAT3 cell-based assay is used to examine the potency of compounds at blocking STAT3 phosphorylation in pancreatic cancer cells. Mia-paca2 cells (ATCC) are grown in DMEM complete medium supplemented with 10% FBS at 37° C. in incubator with 5% $CO_2$. Cells are then collected, counted, plated at $4 \times 10^4$ cells/well in 96-well plates, and cultured for overnight at 37° C. with 5% $CO_2$. Culture medium is removed from the cells and replaced with serum-free medium containing either vehicle alone (DMSO) or 2× final concentrations of compounds across a range from 0-20 µM at 1:3 dilution (10 dilutions). After incubation for an additional 5 hours, 100 microliters of 10 day MIA PACA2 culture supernatant (conditioned medium) are added into the plates to activate STAT3. Cells are treated for an additional 20 minutes at 37° C. in an incubator supplied with 5% $CO_2$. After stimulation, all medium is manually removed as above and cells are lysed in 50 microliters of ice cold 1×MSD lysis buffer (MesoScale Diagnostics, K150DID-2) containing 1×HALT protease and phosphatase inhibitor cocktail ((Thermo Scientific, 78441). The 96-well plates are sealed and then mixed for 2 minutes on an orbital shaker at room temperature, and then immediately frozen at −80° C. overnight. pSTAT3 is detected with the use of the MA6000 MSD Whole Cell Lysate Kit for Phospho-STAT-3 (Tyr 705) (MesoScale Diagnostics, #K150DID-2) as following, plates were blocked with blocking buffer at room temperature for 1-2 hours with shaking, and then washed 4× with washing buffer. Added 25 µl of protein lysate to each well and incubated the plates for additional 1-2 hours. Read the plates with MSD plate reader 6000 after washing plates 4× with the washing buffer, Data are analyzed using the Graph Pad program.

A compound within the scope of the invention is tested in this assay substantially as above. The compound of Example 1 inhibits the phosphorylation of STAT3 with an $IC_{50}$ of 12 nM. These results demonstrate that the compound of Example 1 inhibits the JAK-STAT3 pathway in a pancreatic cancer cell line.

SUM-159-MSD-pSTAT3 Cell-Based Assay

The SUM-159-MSD-pSTAT3 cell-based assay is used to examine the potency of compounds at blocking STAT3 phosphorylation in breast cancer cells. Sum-159 cells (Asterand) are grown and maintained in HAM's F-12 medium (Gibco 11765-054) with 5% FBS, insulin (5 microgram/mL) and hydrocortisone (1 μg/ml). Cells are collected, counted, plated at $4×10^4$ cells/well in 96-well plates, and cultured for overnight at 37° C. with 5% $CO_2$. Culture medium is then removed and replaced with F-12-medium containing either vehicle (DMSO) alone or 2× final concentrations of compounds across a range from 0-20 μM at 1:3 dilutions (10 concentration points). After incubation for five additional hours, medium is removed and cells are treated with 100 microliters of 2× human IL-6 (20 ng/mL diluted in F-12 complete medium) and incubated for an additional 20 minutes at 37° C. in 5% $CO_2$. After stimulation, all medium is manually removed as above and cells are lysed in 50 microliters of ice cold 1×MSD lysis buffer containing 1× HALT protease and phosphatase inhibitor cocktail. The 96-well plates are sealed and then mixed for 2 minutes on an orbital shaker at room temperature, and then immediately frozen at −80° C. overnight. pSTAT3 is detected with the use of the MA6000 MSD Whole Cell Lysate Kit for Phospho-STAT-3 (Tyr 705) (Meso Scale Diagnostics, #K150DID-2) as described above. Plates are read by using a MSD plate reader. Data are analyzed using Graph Pad program.

A compound within the scope of the invention is tested in this assay substantially as above. The compound of Example 1 inhibits the phosphorylation of STAT3 with an $IC_{50}$ of 21 nM. These results show that the compound of Example 1 inhibits the JAK-STAT3 pathway in a breast cancer cell line.

We claim:

1. A compound which is 3-[(1R)-6-fluoro-2,3-dihydro-1H-inden-1-yl]-N-(3-methyl-1H-pyrazol-5-yl)-3H-imidazo[4,5-b]pyridin-5-amine, or a pharmaceutically acceptable salt thereof.

2. The compound according to claim 1 which is 3-[(1R)-6-fluoro-2,3-dihydro-1H-inden-1-yl]-N-(3-methyl-1H-pyrazol-5-yl)-3H-imidazo[4,5-b]pyridin-5-amine.

3. The compound according to claim 1, which is 3-[(1R)-6-fluoro-2,3-dihydro-1H-inden-1-yl]-N-(3-methyl-1H-pyrazol-5-yl)-3H-imidazo[4,5-b]pyridin-5-amine dihydrochloride.

4. A pharmaceutical composition comprising the compound or salt of claim 1, and a pharmaceutically acceptable carrier, diluent, or excipient.

5. A method of treating cancer, comprising administering to a patient in need thereof, an effective amount of the compound or salt of claim 1.

6. The method according to claim 5, wherein the cancer is selected from the group consisting of breast cancer, lung cancer, pancreatic carcinoma, renal cancer, ovarian cancer, prostate cancer, head and neck cancer, hepatocellular carcinoma, and colon cancer.

* * * * *